United States Patent [19]

Tolman et al.

[11] 4,372,755

[45] Feb. 8, 1983

[54] PRODUCTION OF A FUEL GAS WITH A STABILIZED METAL CARBIDE CATALYST

[75] Inventors: Radon Tolman, Evergreen; Frank M. Stephens, Jr., Lakewood, both of Colo.

[73] Assignee: Enrecon, Inc., Golden, Colo.

[21] Appl. No.: 202,319

[22] Filed: Oct. 30, 1980

Related U.S. Application Data

[63] Continuation-in-part of Ser. No. 928,506, Jul. 27, 1978, abandoned.

[51] Int. Cl.³ .............................................. C10J 3/54
[52] U.S. Cl. .................................. 48/197 R; 48/202; 48/209; 48/210
[58] Field of Search ..................... 48/197 R, 202, 206, 48/209, 210; 252/373; 585/733

[56] References Cited

U.S. PATENT DOCUMENTS

| | | | |
|---|---|---|---|
| 1,495,776 | 5/1924 | Burdick | 48/210 |
| 2,113,774 | 4/1938 | Schmalfeldt | 48/202 |
| 2,527,130 | 8/1950 | Hemminger | |
| 2,589,925 | 5/1952 | Cain et al. | |
| 2,694,623 | 11/1954 | Welty et al. | 48/197 R |
| 3,031,287 | 4/1962 | Benson et al. | 48/197 |
| 3,847,567 | 11/1974 | Kalina et al. | 48/202 |
| 4,118,204 | 10/1978 | Eakman et al. | 48/197 R |
| 4,134,907 | 1/1979 | Stephens | 48/197 R |
| 4,184,852 | 1/1980 | Russ | 48/197 R |

OTHER PUBLICATIONS

Burton et al., Levy, Properties of Carbides, Nitrides, Borides, Advanced Materials in Catalysis, pp. 101–127, 1977.
EPRI, "Thermodynamically Stable Forms of Elements in the Hygas Gasifier".
Bulletin of Alloy Phase Diagrams, vol. 2, No. 1, 1981, p. 25.
Kirk–Othmer, Encyclopedia of Chem. Tech., vol. 18, 2nd Ed., 1969, pp. 125–128.

*Primary Examiner*—Peter F. Kratz
*Attorney, Agent, or Firm*—Sheridan, Ross & McIntosh

[57] ABSTRACT

A fuel gas containing methane is produced from a carbonaceous material in a single reaction zone by reacting the carbonaceous material in the presence of a stabilized metal carbide catalyst and water vapor and/or carbon dioxide at a temperature of from about 500° C. to about 900° C. The water vapor and/or carbon dioxide is maintained in an amount of from about 10 to about 30 percent by volume.

27 Claims, 2 Drawing Figures

PRODUCTION OF A FUEL GAS WITH A STABILIZED METAL CARBIDE CATALYST

CROSS REFERENCE TO RELATED APPLICATIONS

This application is a continuation-in-part application of Ser. No. 928,506, filed July 27, 1978 now abandoned.

TECHNICAL FIELD

The present invention relates to a process for producing a fuel gas by reacting in a single reaction zone a carbonaceous material with water vapor in the presence of a stabilized metal carbide catalyst.

BACKGROUND ART

The prior art discloses numerous methods of obtaining hydrocarbon gases from carbonaceous materials, such as those proposed in U.S. Pat. No. 3,775,072, wherein the organic material is reacted under pressure with steam; U.S. Pat. No. 2,759,677 which provides for use of steam generated in the process for reaction with waste materials; U.S. Pat. No. 3,776,150 which uses a fluidized bed for methanation reactions; U.S. Pat. No. 3,817,724 wherein oxygen-free recycle gases are introduced into the combustion zone; and U.S. Pat. No. 3,817,725 wherein methanated gases are recycled to a combustion zone for purposes of transferring sensible heat and increasing methane content in the product.

Many hydrogenation, gasification and methanation processes utilize metals as catalysts. For example, U.S. Pat. Nos. 3,759,677 and 3,817,725 disclose alkali carbonates as preferred gasification catalysts. U.S. Pat. No. 3,817,725 further uses Group VIII metals, such as nickel, either as oxides or sulfides, as catalysts in a methanation zone having a temperature of 500°–1000° F. Catalysts consisting of single metals, including oxides, sulfides or carbonates or mixtures of these, selected from Groups IB, VIB and VIII, in addition to an alkali-type promoter from Group IA, IIA and VII rare earths, are used in a two stage gasification and methanation process of U.S. Pat. No. 3,904,386. U.S. Pat. No. 3,594,305 teaches the use of a two component catalyst system for the hydrogasification of coal at a temperature of 750°–800° F., wherein the first catalyst is selected from Group VIII and is preferably an alloy such as cobalt/molybdenum, nickel/tungsten or nickel/molybdenum and the second catalyst is a noble metal. U.S. Pat. No. 3,505,204 obtains hydrocarbons from carbonaceous materials in a single reactor having a temperature of 800°–1200° F. by using a two component catalyst comprising an alkali metal or alkaline earth metal in conjunction with a Group VIII metal. U.S. Pat. No. 3,847,567 utilizes a Group VIII or an alkali metal as a methane reduction catalyst in a gas reformer of a coal hydrogasification process. U.S. Pat. No. 2,629,728 discloses the use of an iron nitrite catalyst to hydrogenate carbon oxides. Additionally, iron and iron oxide are taught as catalysts in a methanation zone having a temperature of 800°–1200° F. for the production of gaseous fuels by synthesis in U.S. Pat. No. 2,543,759. U.S. Pat. No. 1,495,776 teaches a catalytic process for converting carbonaceous material into gases. Lime is the preferred catalyst; however, other reagents such as calcium, alumina, magnesia, silica, iron, nickel or copper and mixtures thereof may be used.

PRIOR ART STATEMENT

The use of iron carbides as catalysts in gasification processes has also been taught. Stephens in U.S. Pat. No. 4,134,907 teaches a means for enhancing the fuel value of a gas by heating it to a temperature of 600°–1200° F. (315°–650° C.) at a pressure of 1–10 atmospheres to promote the production of carbon from carbon monoxide and hydrogen in the presence of iron. The iron and carbon react to form $Fe_3C$ which in turn reacts with hydrogen to form methane and reform iron.

Russ in U.S. Pat. No. 4,184,852 teaches the use of metal carbide complexes to form methane; however, his process consumes the metal carbide complexes in the methane reactor. Moreover, he forms binary or ternary metal carbides at a temperature of about 2200° F. and a low pressure of about 2 atmospheres and then forms the methane in another reactor maintained at a maximum temperature of 350° F.

Benson, et al in U.S. Pat. No. 3,031,287 form a carburized iron in a reduction stage of their process which is then utilized in an oxidation or methanation stage to aid in the production of a gas mixture comprised of hydrogen, carbon monoxide and methane. Benson, et al, prefer the methanation to be conducted at a temperature of 1000°–1200° F.

U.S. Pat. No. 2,527,130 to Hemminger discloses the addition of small amounts of silicon to iron type catalysts used in the production of liquid hydrocarbons in order to reduce the tendency of the catalyst to carbonize. The temperature of the Hemminger process for the production of synthetic liquids is about 650° F., and it is conducted in a manner to avoid the formation of methane and to enhance the formation of butane and higher hydrocarbons.

U.S. Pat. No. 2,589,925 teaches a hydrocarbon synthesis process conducted at a temperature of 550°–750° F. which utilizes an iron catalyst preconditioned with carbon monoxide to form mainly $Fe_2C$ in order to prevent non-carbide carbon formation on the catalyst. This reference further discloses maintaining a sufficiently high hydrogen partial pressure in order to impair the formation of non-carbide carbon on the catalyst.

The prior art teaches the use of Group VIII metals, including iron carbides, an methanation catalysts or reactants at temperatures that are generally less than 1200° F. (650° C.) in order to produce methane in relatively high amounts. Generally, as temperature increases, the production of methane decreases. Moreover, many of the methanation catalysts of the prior art will act as methane reforming catalysts at temperatures of greater than about 1300° F. (705° C.), e.g., U.S. Pat. No. 3,847,567, and/or will lose catalytic activity, e.g., due to oxidation, at temperatures of about 1200° F. (650° C.) and higher. The prior art does not combine in one reactor the gasification of a carbonaceous material with the methanation of the gas produced by the gasification of the carbonaceous material, because the temperatures for gasification are not generally conducive to methanation. In order to obtain adequate rates of gasification of carbonaceous material, a minimum temperature of about 500° C., with over 800° C. being preferred, is usually used. Moreover, many of the prior art catalysts are active site catalysts, e.g., nickel, cobalt, vanadium and molybdenum, which are prone to sulfur poisoning.

The stabilized metal carbide catalysts of the present invention maintain their catalytic activity at temperatures exceeding 650° C. and, therefore, can be used in a combined gasification and methanation reactor for the production of a synthetic gas having a relatively high methane content from carbonaceous material. Although generally the temperatures required for gasification will reduce methane production, the gasification of the carbonaceous material, e.g., coal, will cause the formation of some methane by the volatilization of higher hydrocarbons than methane. These volatilized higher hydrocarbons react with hydrogen to form methane. Moreover, the stabilized metal carbide catalysts are active methanation catalysts at much lower carbon levels than those of conventional metal carbides such as cementite, $Fe_3C$, and they are not poisoned by the presence of gaseous sulfur compounds.

Additionally, the process of the present invention can utilize untreated water and/or effluents, unsuitable for use in a boiler, to generate steam by means of heat from product gas being cleaned by the water. Process char can be used to heat the steam and recycle gases to create a heat-efficient, thermoneutral reaction.

DISCLOSURE OF THE INVENTION

The present invention provides a process for production of a fuel gas from organic materials, such as coal and solid municipal waste. The produced fuel gas contains greater than 8 mole percent methane, and greater than 30 mole percent under preferred conditions, in addition to carbon monoxide, carbon dioxide and hydrogen. The carbonaceous material is reacted in a chemically active fluid bed in the presence of hydrogen, carbon monoxide, steam and a stabilized metal carbide catalyst. The stabilized metal carbide may be added to the reactor directly or it may be formed in the reactor by the deposition of carbon on the stabilized metal to form surface carbides. The stabilized metal carbide catalyst remains catalytically active at gasification temperatures which exceed about 650° C. (1200° F.), thereby allowing the gasification and methanation processes to be conducted in a single reaction zone.

The term "stabilized" as used herein in reference to a metal carbide catalyst refers to the ability of the catalyst to maintain its catalytic activity, including its physical integrity, under gasification conditions and it primarily refers to an oxidation resistant metal carbide catalyst. The term is not intended to imply total chemical stability or inertness, because the stabilized metal carbide catalyst must have the ability to act as a bulk chemical catalyst, actively partaking in the formation of methane. The stabilized metal carbide catalyst must be sufficiently chemically active to enable it to accept carbon, e.g., to enable the stabilized metal to be carbided, and sufficiently chemically active to transfer carbon to hydrogen to form methane. In accepting carbon from carbon monoxide, the stabilized metal also accepts oxygen which is subsequently transferred to carbon monoxide resulting in the formation of carbon dioxide. Thus, the stabilized metal catalyst is continuously carbided and decarbided.

The deposition of carbon on the stabilized metal carbide and/or the stabilized metal within the reactor is dependent upon the interaction of the contact of the stabilized metal catalyst with the carbonaceous feed material, the Boudouard reaction ($CO_2 + C \rightleftharpoons 2CO$) and the steam carbon reaction ($C + H_2O \rightleftharpoons CO + H_2$). Carbon monoxide, e.g., produced by the steam carbon reaction, reacts readily with steam to produce carbon dioxide via the water gas shift reaction ($CO + H_2O \rightleftharpoons CO_2 + H_2$). The carbon dioxide aids in maintaining the equilibrium of the Boudouard reaction toward the production of carbon monoxide. Therefore, carbon deposition and carbide formation can be controlled by the addition of water vapor and/or carbon dioxide to the fluidized bed reactor. Thus, water vapor and/or carbon dioxide is continuously added to the fluid bed in an amount of from about 10 to about 30 volume percent of the gas contained in the reaction zone. The steam carbon and Boudouard reactions are endothermic, and they can influence the carbon deposition and carbide formation as a function of temperature. Moreover, since the presence of either two much water vapor and/or carbon dioxide can cause excessive oxidation of the stabilized metal catalyst resulting in a loss of its methanation activity, the resistance to oxidation of the stabilized metal carbide catalyst is also controlled by temperature and/or the amount of water vapor or carbon dioxide present.

The methanation reaction and the side reactions producing carbon dioxide are highly exothermic, whereas the reactions producing carbon monoxide and hydrogen from the organic feed materials and steam are endothermic. Combining these reactions in a single system provides a very nearly thermoneutral overall reaction approaching the following:

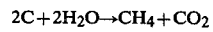

$$2C + 2H_2O \rightarrow CH_4 + CO_2$$

This combination provides most of the heat required to gasify the organic feed material and increases overall thermal efficiency of the process. Overall thermal efficiency can be further increased by using the sensible heat in the off-gas to produce steam by direct contact with water being fed into the system and by further heating this steam and an inlet gas stream to a temperature above the temperature of the gasification/methanation reaction zone.

The gasification/methanation reaction zone is composed of a reactor bed containing a catalytic bed material of the stabilized metal carbide particles, sized to prevent the agglomeration and caking of the organic feed. A fluidized bed is preferred as it provides isothermal operation, high surface area for catalysis and permits control of particle residence time.

Hydrogen for hydrogasification of the carbonaceous feed material can be produced by heating a recycle gas stream, using the sensible heat in the reactor off-gas and hot gases from char combustion, to a temperature over 800° C., thereby shifting the composition of the recycled gas to higher levels of hydrogen and carbon monoxide by reforming the methane with water vapor. The sensible heat in the recycled gas also helps provide the heat required to raise the carbonaceous feed material to gasification temperature. Thus, the ratio of hydrogen, carbon monoxide, methane, water vapor and carbon dioxide must be properly maintained within the gasification/methanation reactor to maintain the catalytic activity of the stabilized metal catalyst and to maintain a desirable production level of methane.

PREFERRED MODE FOR CARRYING OUT THE INVENTION

Figure 1:
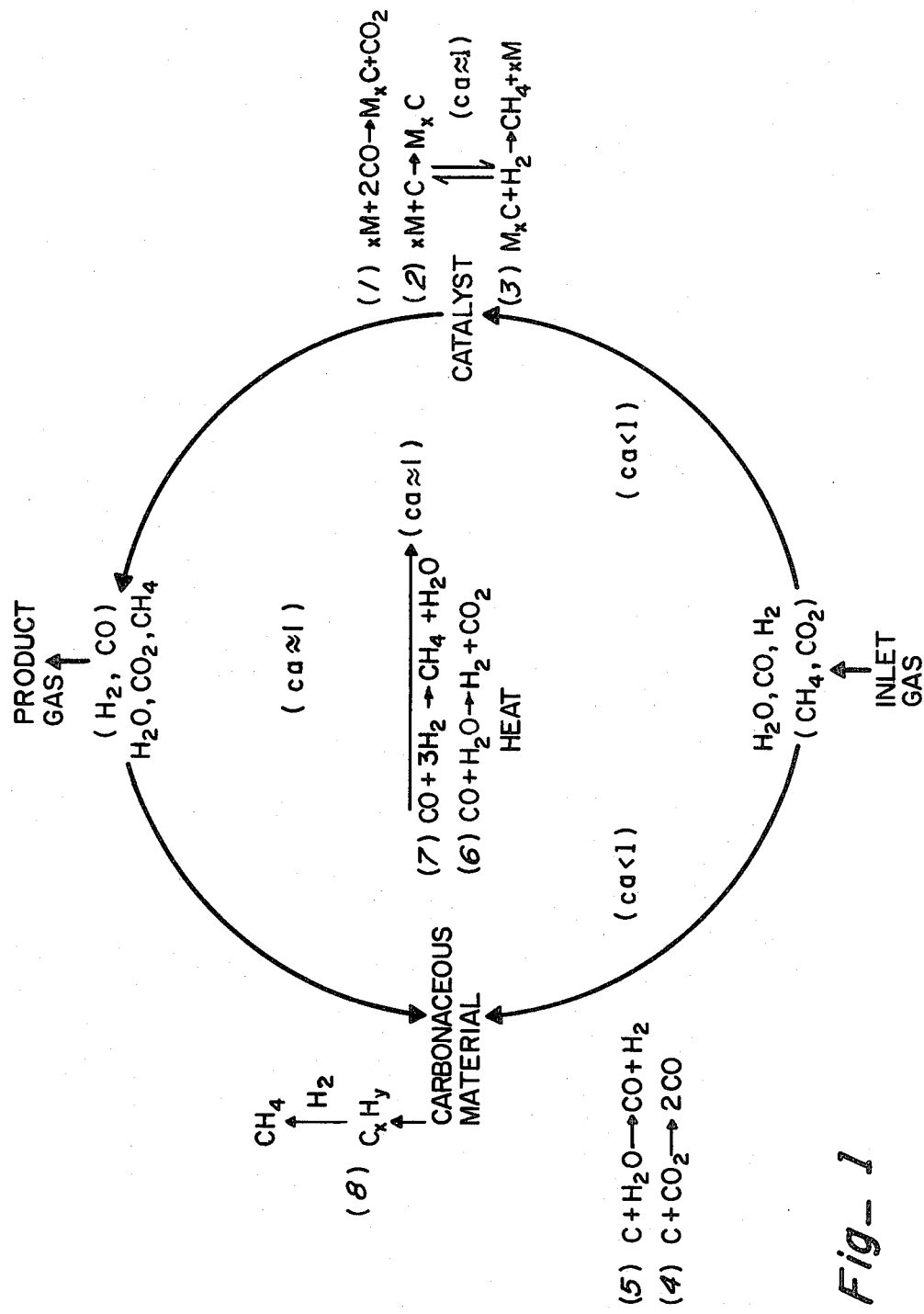
FIG. 1 is a schematic representation of the primary reactions involved in a combined gasification/methanation process utilizing a stabilized metal carbide catalyst.

The process of the present invention entails the use of a stabilized metal carbide as a catalyst in the production of fuel gas by synthesis. Depending upon the carbonaceous feedstock, a wide variety of fuel gases can be produced including a medium Btu (British thermal unit) fuel gas having a Btu value of greater than about 300 Btu per cubic foot for gas turbine fuel, synthetic natural gas and synthesis gas for methanol or gasoline production. The process can be operated at a thermal efficiency of greater than 80 percent while producing a fuel gas which can have a Btu value of over 400 Btu per cubic foot of fuel gas. The carbonaceous material can be any of a number of carbon containing materials which are combustible, for example, peat and lignite, subbituminous, bituminous and anthracite coals and solid municipal and industrial waste.

Although the exact mechanism of action of the stabilized metal carbide catalyst is not known, it is thought that the stabilized metal carbide catalyst is acting primarily as a bulk catalyst which acts as an intermediate in the chemical reaction(s) being catalyzed and is present in its original concentration at the end of the reaction(s). The stabilized metal carbide catalyst may also be acting as an active site catalyst which does not partake in the chemical reaction(s) being catalyzed but wherein the surface of the catalyst provides a site for reaction of the reactants. Because the stabilized metal carbide catalysts of the present invention maintain their activity in the presence of sulfur, they are not susceptible to sulfur poisoning and it appears that they act primarily as bulk catalysts. Therefore, for simplicity in describing this invention, the activity of the stabilized metal carbide catalyst will be described in terms of a bulk catalyst, although, it must be remembered that they may also be acting as active site catalysts.

The stabilized metal carbide catalyst is comprised of two components, carbon and an alloy of at least two different metals, each of which is capable of forming a metal carbide. More specifically, the catalyst is defined as a composition of these components which has a free energy of formation of from about $-30,000$ to about 10,000 British thermal units per pound atom of carbon at a temperature of from about 500° to about 900° C. and a pressure from about 100 to about 8,300 kilopascals (about 15 to about 1200 p.s.i.a.) and preferably a temperature from about 750° C. to about 900° C. and preferably a pressure from about 1,000 to about 4,000 kilopascals (about 150 to about 600 p.s.i.a.).

Each of the metals which comprise the alloy component must have the ability to form a metal carbide at the process conditions of the gasification/methanation reaction zone. Examples of suitable metals include, iron, silicon, manganese, cobalt, chromium, nickel, aluminum, vanadium, tungsten, molybdenum, calcium, boron, sodium and magnesium. It is preferred that one or both metals be selected from the group consisting of silicon and those metals which form intermediate carbides (carbides which are intermediate in character between ionic and interstitial carbides), i.e., iron, cobalt, chromium, manganese and nickel. The intermediate carbides tend to be more chemically active than interstitial carbides and tend to exhibit a greater physical stability and chemical stability, e.g., with respect to oxidation, than ionic carbides.

With respect to a particular stabilized metal catalyst, the particular alloy component should be comprised of metals which exhibit a relative difference in free energy of formation of the carbides of each metal such that one metal forms a sufficiently stronger carbide to act as a stabilizing component thereby enhancing the chemical activity of the other metal carbide. It is preferred that there be a difference in free energy of formation between at least two of the metal components of the alloy of at least about 5,000 British thermal units per pound atom of carbon. Additionally, the effects of combining two or more metals to form the alloy or stabilized metal component of the catalyst results in the alloy having a lower capability for carburization and oxidation than each of the metals separately. Moreover, the alloy appears to exhibit metastable oxidation states thereby allowing for its absorption and desorption of both carbide and oxygen.

Examples of stabilized metal carbide catalysts include iron silicide carbide, manganese chromium carbide, ferrochromium carbide and manganese cobalt carbide.

One group of preferred stabilized metal carbide catalysts is iron silicide carbide catalysts containing from about 4 to about 50 weight percent of silicide or silicon and from about 0.5 to about 3.0 weight percent of carbon by weight of the catalyst. With respect to iron silicide carbides, it is preferred that the catalyst contain less than about 32 weight percent of silicon, because within this range the catalyst is magnetic allowing for its more convenient separation from elutriated char and ash for subsequent reuse. Moreover, as long as the iron silicide carbide catalyst contains a sufficient amount of silicon to maintain its stability, then generally the more iron present in the catalyst, the greater its catalytic activity. It is more preferred that an iron silicide carbide catalyst contain from about 10 to about 20 percent by weight of silicon. At silicon levels less than about 4 percent, the catalyst looses its stability at temperatures greater than about 650° C. At silicon levels greater than about 50 percent, the silicon impedes the surface carburization of the iron silicide preventing the formation of the iron silicide carbide catalyst. If an iron silicide carbide catalyst has a carbon level less than about 0.5 percent by weight, the catalyst is not sufficiently active. Since the maximum carbide content of an iron silicide is about 3 percent, any carbon present on the catalyst which is above about 3 percent will be in the form of elemental carbon, not as a surface carbide. Silvery pig iron, which generally contains from about 0.5 to about 1.5 percent carbon, from about 12 to about 20 percent silicon and from about 82 to about 84 percent iron by weight, is an example of a preferred iron silicide carbide catalyst.

The catalyst is employed in a fluidized bed reactor which has a single reaction zone for the production of fuel gas. The stabilized metal carbide catalyst employed in the reaction zone is sufficiently physically stable and dense to remain in the bed during the gasification of many tons of feed material, requiring only makeup as a result of elutriation and sulfidation. The amount of catalyst required in a particular system is dependent upon the temperature of the fluidized bed, time of contact with the carbonaceous material and the reactivity of the carbonaceous material. There should be a sufficient amount of the stabilized metal carbide catalyst in the reaction zone to prevent caking and agglomeration of the carbonaceous materials and provide adequate surface area for catalysis. Therefore, it is preferred that the catalyst be present in a greater amount than the amount of fresh, unreacted (as opposed to char) carbonaceous material. For example, a suitable mixture in the reactor may comprise about four parts by weight of the stabilized metal carbide catalyst to about one part by weight of fresh carbonaceous material.

The particle size of the catalyst is such as to prevent caking and agglomeration of materials in the fluidized bed. Generally, the particle size of the catalyst should be compatible with the space velocity required for its fluidization in the reaction zone.

The catalyst may be added directly to the reactor or it may be formed in the reactor. It can be formed in the reactor by the addition of the metal alloy component to the reactor and the deposition of carbon in amounts which are sufficient to form a stabilized metal carbide having a free energy of formation of from about −30,000 to about 10,000 British thermal units per pound atom of carbon at the gasification/methanation conditions of the process. The carbon should be in a reactive form, for example, carbon produced from a gaseous reaction.

The gasification of a carbonaceous material and/or the methanation of a gas involves a number of dynamic and interrelated chemical reactions. Heretofore, the prior art has separated gasification and methanation reactions in order to utilize different conditions to affect the separate chemical reactions involved in gasifying a carbonaceous material and those reactions involved in forming methane. Although the process of the present invention can be used to gasify carbonaceous material or to increase the methane value of a gas containing hydrogen and carbon monoxide, the essence of the invention lies in balancing the equilibriums and/or kinetics of the chemical reactions to allow for the gasification and methanation of a carbonaceous material to occur within the same reactor while maintaining the catalytic activity of a stabilized metal carbide catalyst. The primary reactions involved in a combined reaction zone are those relating to the gasification of carbon, the water gas shift reaction, the carbiding and decarbiding of the catalyst acting as a bulk catalyst, the oxidation and reduction of the catalyst acting as a bulk catalyst, and the formation of methane. A schematic representation of these reactions is presented in FIG. 1. Since the optimization of some of the reactions is detrimental to others in the reaction zone, it is necessary to control the kinetics and equilibriums of the chemical reactions involved in order to maximize methane production while still obtaining adequate gasification of the carbonaceous material. The control is a function of the ratio of gases present, temperature, pressure and catalyst used. The kinetics and equilibriums of the chemical reactions are preferably controlled primarily by temperature and the addition of water vapor and/or carbon dioxide. The chemical interactions can be explained with reference to FIG. 1. (The numbers used to depict the reactions are for reference purposes only and are not indicative of the order of occurrence. Additionally, "M", as used in the figure, refers to the metal alloy component of the catalyst).

In FIG. 1, an inlet gas comprising primarily water, hydrogen and carbon monoxide with lesser amounts of methane and carbon dioxide is injected into a reaction zone containing a source of carbon, e.g., a carbonaceous material, and a stabilized metal carbide catalyst, $M_xC$. The carbon activity (ca) of the gases contained within the reaction zone will vary from a value less than one to approximately one depending upon the location in the reaction zone. The carbon activity of a gas is an equilibrium value which denotes the ability of the gas to form elemental carbon. A value of one represents equilibrium, at a value greater than one the gas will tend to form elemental carbon and at a value of less than one the gas will tend to consume elemental carbon. The inlet gas will have a carbon activity of less than one enabling its water and carbon dioxide components to readily react with the carbon from the carbonaceous material, including char, causing the gasification of the carbon by the formation of carbon monoxide and hydrogen, reactions (4) and (5). Since the stabilized metal carbide catalyst is not readily oxidized at reaction conditions, the inlet gas will preferentially oxidize the carbonaceous material as long as the concentrations of water and/or carbon dioxide are not excessive, e.g., greater than about 30 volume percent of the gas in the reaction zone. The presence of hydrogen in the inlet gas and from reaction (5) allows for the decarburization of the stabilized metal carbide catalyst, reaction (3), thereby forming the desired methane. The stabilized metal alloy is carbided in accordance with reactions (1) and (2). To a lesser extent, methane is also formed by the reaction of carbon or a source of carbon, e.g., carbon monoxide, with hydrogen, reaction (7). The production of any significant quantity of methane from reaction (7) occurs to the extent that the stabilized metal carbide catalyst is acting as an active site catalyst. The carbon monoxide reacts with water vapor to form hydrogen and carbon dioxide, reaction (6). The heat given off in the formation of carbon dioxide and methane provides most of the heat necessary for gasifying the carbonaceous material.

The presence of water, in the form of steam, aids the gasification of elemental carbon. Since the kinetics of the reactor are controlled, mainly by temperature, any inlet gas, e.g., recycle gas or feed gas, added to the process will be at least the temperature of the gasifier, about 500° to about 900° C., and preferably of a sufficient temperature to maintain the reactor at the preferred temperature for a particular process. At these temperatures, a portion of the carbonaceous material readily volatilizes in the form of higher hydrocarbons which react with hydrogen to form methane, reaction (8). The product gas comprising carbon dioxide, methane and water is continuously removed from the process.

Thus, FIG. 1 represents the favored primary reactions of the process. However, since all of the reactions portrayed are reversible, their equilibriums are shifted toward the forward reactions by the addition of carbonaceous material, water vapor, hydrogen and carbon monoxide. Carbon dioxide can be used in place of or in conjunction with water vapor. Water vapor is preferred to carbon dioxide because it is more easily produced within the process, for example, through a recycle gas stream, and it supplies a source of hydrogen. The source of water vapor is not critical and it can be from the carbonaceous material and/or the inlet gas, e.g., a recycle gas or feed gas. Although the addition of water vapor (or carbon dioxide) to the reactor is not narrowly critical, it cannot be so great to cause excessive or rapid oxidation of the stabilized metal carbide catalyst. Therefore, water vapor and/or carbon dioxide is maintained in the reactor in an amount from about 10 to about 30 volume percent of the gas used in the reactor. At water vapor and/or carbon dioxide levels of less than about 10 volume percent excess carbon deposition will occur which can cause plugging of the off-gas system. Water vapor and/or carbon dioxide levels greater than about 30 volume percent will tend to cause excessive oxidation of the catalyst. However, within this recited range, generally as the temperature of the reactor is increased, the more water vapor and carbon dioxide which can be present.

The additional source of hydrogen and carbon monoxide supplied to the reactor may be a recycle gas stream from a portion of the product gas. In such an application, it is preferred that the recycled product gas be reformed, by the addition of heat, water and a reforming catalyst, to higher levels of carbon monoxide and hydrogen which is recycled into the reaction zone. The reforming catalyst is a steam hydrocarbon reforming catalyst and any such catalyst active at these conditions may be used. Examples of such catalysts include Group VIII metals, for example, nickel, nickel oxide and chromium oxide. The gasification of the carbonaceous material results in the formation of char which can be removed and combusted in a separate combustor. The heat from the combustor can be used in the reformation of the product gas which can then be recycled to the reactor.

Temperature and pressure are also used to favorably balance the equilibriums and the kinetics of the reactions. The temperature must be sufficient to cause the gasification of the carbonaceous material but not so high so as to substantially reduce methane equilibrium. Therefore, the temperature is a function of the reactivity of the particular carbonaceous feed material and the desired methane content of the produced fuel gas. Thus, the temperature of the reactor will be from about 500° C. to about 900° C. The more reactive the carbonaceous material is, generally, the lower the temperature of the process and the more methane the fuel gas will contain. Hence, the process temperature required for peat will be lower than that required for a lignite coal which is lower than that required for bituminous coal which is lower than that required for anthracite coal. For example, if the carbonaceous feed is a peat, the temperature of the process could be about 500° C., its gasification temperature, whereas, the temperature of the process for a bituminous coal would be from about 760° C. to about 870° C., its gasification temperature. Peat, therefore, has a greater potential for producing greater amounts of methane compared to a bituminous coal. A preferred temperature of a particular process is the threshold temperature at which the carbide form of the stabilized metal carbide catalyst is more stable than its oxidized form. Threshold temperature is defined as the temperature range at which the carbide activity of the catalyst, i.e., the activity of the carbide form of the catalyst relative to the oxidized form of the catalyst, just exceeds a value of one. The carbide activity of the catalyst is an equilibrium value, wherein a value of one represents equilibrium and a value greater than one represents a greater tendency of the catalyst to be in a carbided form as opposed to an oxidized form. Within the process conditions heretofore described, e.g., temperature, pressure, and amount of water vapor, the threshold temperature of a particular process is primarily dependent upon the particular stabilized metal carbide catalyst. For example, when silvery pig iron is the stabilized metal carbide catalyst, the threshold temperature will be from about 775° C. (1425° F.) to about 845° C. (1550° F.).

The pressure of the process can vary over a wide range of from about 100 kilopascals (15 p.s.i.a.) to about 8,300 kilopascals. However, a pressure of 1,000 kilopascals (150 p.s.i.a.) to about 4,000 kilopascals (600 p.s.i.a.) is preferred.

Figure 2:
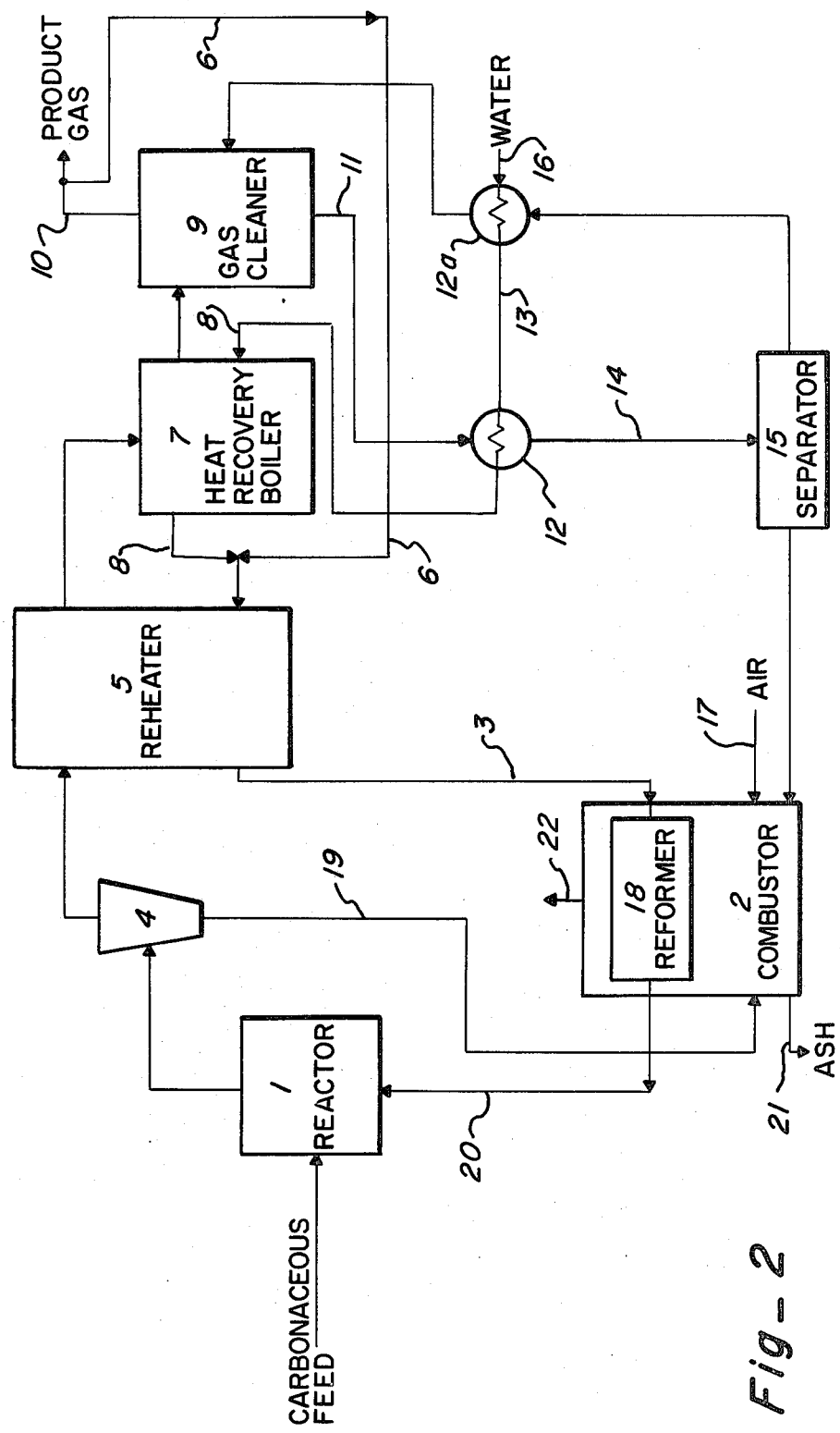
FIG. 2 is a flow diagram for a process which combines gasification of a carbonaceous material and methanation of its gas in the presence of a stabilized metal carbide catalyst.

The stabilized metal carbide catalyst is useful in any process for synthesizing hydrocarbon gases from carbonaceous sources. It is especially useful in those processes wherein heat is taken from the produced gas and is used to heat water to produce steam and to reheat a portion of the produced gas which is recycled in the process and wherein the char produced in the process is combusted and the heat produced therefrom is used to further heat the recycle gas in order to reform the methane contained therein to carbon monoxide and hydrogen. Preferred processes utilize fluidized bed reactors. A general process of this type is shown in FIG. 2. In the process of FIG. 2, carbonaceous feed material is introduced into reactor 1 wherein it is reacted in a single reaction zone consisting of a fluidized bed comprised of unreacted carbonaceous feed material and a catalytic bed material comprised of a stabilized metal carbide and a process recycle gas stream 3 which is reheated by the combustor gases prior to entry into reactor 1. The off-gas produced in reactor 1 is then conducted to separator 4 wherein the particulate matter is removed. The particulate free off-gas is then conducted to reheater 5 wherein the temperature of the off-gas is reduced from a temperature from about 500° C.–900° C. to a temperature of about 400° C.–750° C. by indirectly heating recycle gas stream 6 having a temperature from about 90° C.–325° C. to a temperature of about 400° C.–825° C. The reactor off-gas is then conducted from reheater 5 to a heat recovery boiler 7 where it is further cooled to a temperature of about 200° C.–550° C. by the indirect heating of water vapor stream 8.

The reactor off-gas then passes from heat recovery boiler 7 to gas cleaner 9 wherein any tar or water contained with the gas are separated from the product gas 10. The tar and water are removed from gas cleaner 9 via conduit 11. The tars and water 11 are cooled in heat exchanger 12 from a temperature of from about 200° C.–550° C. to a temperature of about 100°–300° C. by the indirect heating of water stream 13. The cooled tar and water stream 14 undergoes separation in separator 15. The water from separator 15, which is directed through heat exchanger 12a where its temperature is further reduced to about 70°–90° C. by indirect heating with water stream 16, can be recycled to gas cleaner 9 for reuse.

The non-water materials from separator 15, e.g., tars, and the particulate matter 19 from separator 4 are added to combustor 2 wherein they are combusted in the presence of air (or another source of oxygen) 17 at a temperature of from about 950° C. to about 1650° C. The combustor gases 22 and ash 21 are removed from the combustor.

The water for reactor 1 is supplied through recycle gas stream 3. Water 16 is introduced into the process and is subsequently heated in exchangers 12 and 12a and then introduced into heat recovery boiler 7 as water stream 8. The water stream 8 is further heated in heat recovery boiler 7 to a temperature of from about 200° to about 350° C. after which it is combined as saturated steam with recycle gas stream 6 and introduced into reheater 5 where they are heated to a temperature of about 400°–825° C. The combined recycle gas stream 3 is introduced into reformer 18 where it is reformed to higher levels of carbon monoxide and hydrogen. It is preferred that the recycle gas stream be reformed by increasing its temperature to about 850° C.–1100° C. at a pressure of from about 1,725–2,750 kilopascals in the presence of a steam hydrocarbon reforming catalyst. The reformation of the recycled gas stream with water vapor need not be performed in the combustor 2. However, the combustor supplies a ready source of heat. Reformed recycle gas stream 20 is introduced into reactor 1 to provide carbon monoxide, hydrogen and water to reactor 1.

Since a process for the combined gasification and methanation of a carbonaceous feed material in the presence of a metal stabilized carbide catalyst is preferably conducted in a manner which is heat efficient, there are a wide variety of changes which could be made in the flow diagram of FIG. 2. For example, a portion of the recycled product gas stream might be used to preheat the carbonaceous feed material prior to its injection into reactor 1. The water added to the system, i.e., water 16, could be heated externally from the process or converted to steam by direct contact of the water stream 16 with a portion of the hot reactor off-gas or product gas. Since air being added to a combustor is generally preheated, air 17 might be preheated externally from the process or by heat produced in the process, e.g., heat of the stack gases. Depending upon the nature of the carbonaceous feed material, product gas 10 may be subjected to an acid removal step. If an acid removal step is included, it would be preferable that the recycled gas stream 6 be taken from the acid cleaned product gas.

EXAMPLE 1

A gas representative of one produced by a carbonaceous material and having a composition of 6.3 percent carbon dioxide, 33.4 percent carbon monoxide, 4.8 percent methane and 55.5 percent hydrogen was used to fluidize a 2 inch continuous fluid bed reactor containing the gas and different catalysts. (All percentages of gases given in the examples are volume percent). Steam was also present in the gas in an amount of about 0.3 volume percent or less by volume of fluidizing gas to control the deposition of carbon. Because a carbonaceous material was not being gasified, it was not necessary that water vapor and/or carbon dioxide be present in the reactor in an amount of from about 10 to about 30 volume percent. The bed was maintained at a pressure of 100 psig (690 kilopascals) and a temperature of 700° C. The composition of the catalyst used in each run is given in Table 1 as is the volume percent of methane in the produced off-gas, the actual contact time between the gas and catalyst and the rate of methanation. The volume percent of methane is based on the equilibrium gas composition normalized to 100 percent by volume on a dry basis.

TABLE 1

| Catalyst Composition | % $CH_4$ in Off-gas | Gas-catalyst Contact Time, min. | Rate % $CH_4$/min. |
|---|---|---|---|
| 46.8 Fe 46.0 Si 2.0C | 31 | 18.1 | 1.73 |
| *46.8 Fe 46.0 Si 2.0C | 35 | 12.0 | 2.92 |
| 69.1 Fe 27.0 Si 2.9C | 35 | 15.4 | 2.27 |
| *82.3 Fe 15.1 Si 0.7C | 32 | 6.0 | 5.27 |
| 89.3 Fe 6.1 Si 1.6C | 35 | 4.6 | 7.61 |

TABLE 1-continued

| Catalyst Composition | % $CH_4$ in Off-gas | Gas-catalyst Contact Time, min. | Rate % $CH_4$/min. |
|---|---|---|---|
| 24 Fe 68 Cr 6.2C | 24 | 7.4 | 3.24 |

*Composition of the catalyst at the beginning of the test, about 3% of carbon was present at the end of the test (a portion of the 3% carbon may have been in elemental form).

EXAMPLE 2

A gas comprising 3 parts hydrogen and 1 part carbon monoxide was used to fluidize a 2 inch continuous fluid bed reactor containing the gas and different catalysts. Steam was also present in the gas in the amount indicated in Table 2. Because a carbonaceous material was not being gasified, it was not necessary that water vapor and/or carbon dioxide be present in the reactor in an amount of from about 10 to about 30 volume percent. The bed was maintained at a pressure of 100 psig (690 kilopascals) and a temperature of 700° C. The composition of the catalyst used in each run is given in Table 2 as is the volume percent of methane in the produced off-gas, the actual contact time between the gas and catalyst and the rate of methanation.

TABLE 2

| Catalyst Composition wt, % | Steam Vol, % | % $CH_4$ in Off-gas | Gas-catalyst Contact Time min. | Rate % $CH_4$/ min. |
|---|---|---|---|---|
| 76.6 Mn 21.2 Cr 4.4C | 0.99 | 40 | 6.04 | 6.62 |
| 67.5 Mn 22.2 Co 2.6C | 0.74 | 33 | 3.8 | 8.81 |
| $SiO_2$ (sand) | 10.0 | 10 | 10.1 | 0.99 |
| *$Fe_3O_4$ $FeSiO_3$ | 0.74 | 15 | 26.5 | 0.54 |

*Obtained from an excess oxidation of an iron silicide carbide catalyst.

EXAMPLE 3

A gas comprising 32.2 percent hydrogen, 3.5 percent carbon monoxide, 10.3 percent carbon dioxide and 54.0 percent methane was used to fluidize a two inch continuous fluid bed reactor containing the gas and iron carbide as cementite, $Fe_3C$. Steam was also present in the gas in an amount of about 10 volume percent or less by volume of the fluidizing gas. The fluidized bed was maintained at a pressure of 100 psig (690 kilopascals) and a temperature of 700° C. After the reactor reached stabilized conditions, the off-gas comprised 7.5 percent nitrogen (nitrogen was used to initially purge the reactor), 46.0 percent hydrogen, 33.5 percent methane, 6.9 percent carbon monoxide and 0.8 percent carbon dioxide. A Mossbauer analysis of the composition of the iron carbide was taken prior to initiating the reactor (Starter Bed) and after the completion of the reactor run (Final Bed) and the compositions are given below in Table 3.

TABLE 3

| Compound | Starter Bed (wt %) | Final Bed (wt %) |
|---|---|---|
| $Fe_3C$ | 72.1 | 91.8 |
| $Fe_3O_4$ | 3.5 | 2.1 |
| $Fe_2O_3$ | 3.5 | 0 |
| FeO | 0 | 0 |
| Fe | 10.5 | 0 |

EXAMPLE 4

A gas comprising 34.8 percent hydrogen, 19.2 percent carbon monoxide, 32.0 percent carbon dioxide and 14.0 percent methane was used to fluidize a two inch continuous fluid bed reactor containing the gas and iron carbide as cementite, Fe₃C. Steam was also present in the gas in an amount of about 20 volume percent of the fluidizing gas. Additionally, carbon dioxide was added intermittently throughout the reaction in order to maintain the volume percent of water and carbon dioxide at a level of about 35 percent by volume of the fluidizing gas. The bed was maintained at a pressure of 100 psig (690 kilopascals) and a temperature of 700° C. The reactor off-gas obtained a maximum of 33.9 percent methane and then the methane content decreased, apparently as a result of the decomposition of the catalyst which is shown by the Mossbauer analyses of the composition of the iron carbide in Table 4.

TABLE 4

| Compound | Starter Bed (wt %) | Final Bed (wt %) |
|---|---|---|
| $Fe_3C$ | 91.8 | 42.4 |
| $Fe_3O_4$ | 2.1 | 26.1 |
| $Fe_2O_3$ | 0 | 0 |
| FeO | 0 | 25.5 |
| Fe | 0 | 0 |

EXAMPLE 5

Fuel gases were produced from Illinois No. 6 coal, a bituminous coal containing about 3.45 percent by weight sulfur, by fluidizing the coal with a gas comprising about 7-7.5 percent carbon dioxide, about 34.8 percent carbon monoxide, about 4.2 percent methane and about 53.9 percent hydrogen and gasifying the coal, constituting about 5 weight percent of the fluidizing gas, at a temperature of about 700° C. and a pressure of about 100 p.s.i.g. in the presence of an iron silicide carbon catalyst. Steam was maintained in the reactor in an amount of from about 6 to about 10 percent by volume of the fluidizing gas. In sample 1, the iron silicide carbon catalyst was produced in the reaction vessel by the carbiding of an iron silicide comprising about 50 weight percent iron and about 50 weight percent silicon. In sample 2, the iron silicide carbide catalyst comprised, at the beginning of the reaction process, about 82 weight percent iron, about 16 weight percent silicon and about 0.6 weight percent carbon. The actual contact time between the gas and catalyst in sample 1 was about 6 minutes and the equilibrium composition of the fuel gas produced was about 1.1 percent nitrogen, about 55.5 percent hydrogen, about 21.5 percent methane, about 15 percent carbon monoxide and about 7.4 percent carbon dioxide. The rate of methanation in sample 1 was about 3.62 percent methane per minute.

The actual contact time between the gas and the catalyst of sample 2 was about 7.44 minutes and the equilibrium gas composition of the fuel gas produced was about 1.5 percent nitrogen, about 31 percent hydrogen, about 44 percent methane, about 17.5 percent carbon monoxide and about 5.5 percent carbon dioxide. The rate of methanation for sample 2 was about 5.94 percent methane per minute.

What is claimed is:

1. A process for the production of a fuel gas from a solid carbonaceous material comprising reacting in a single reaction zone the solid carbonaceous material in the presence of a stabilized metal carbide catalyst capable of substantially maintaining its physical integrity and chemical activity under gasification conditions, said catalyst comprising carbon and a metal alloy and having a free energy of formation of from −30,000 to 10,000 British thermal units per pound atom of carbon at the reaction conditions, said metal alloy comprising at least two metals selected from the group consisting of iron, silicon, manganese, cobalt, chromium, nickel, aluminum, vanadium, tungsten, molybdenum, calcium, boron, sodium and magnesium wherein one of said two metals forms a sufficiently stronger carbide to act as a stabilizing component thereby enhancing the chemical activity of the other metal carbide and a gas of which from about 10 to about 30 volume percent is selected from the group consisting of water vapor, carbon dioxide and mixtures thereof at a temperature and pressure sufficient to cause the gasification of the carbonaceous material and cause the formation of a sufficient amount of methane to produce a fuel gas wherein the temperature is from about 500° C. to about 900° C. and the pressure is from about 100 kilopascals to about 8300 kilopascals.

2. The process of claim 1 wherein the relative difference of at least two of the metals in their free energy of formation of their respective carbides is at least 5,000 British thermal units per pound atom of carbon.

3. The process of claim 1 wherein the temperature of the reaction zone is within the threshold temperature range of the stabilized metal carbide catalyst.

4. The process of claim 1 wherein the stabilized metal carbide catalyst is selected from the group consisting of iron silicide carbide, manganese chromium carbide, ferrochromium carbide and manganese cobalt carbide.

5. The process of claim 4 wherein the stabilized metal carbide catalyst is an iron silicide carbide.

6. The process of claim 5 wherein the stabilized metal carbide catalyst comprises from about 4 to about 50 weight percent silicon, from about 0.5 to about 3 weight percent carbon and the remainder of the catalyst comprises primarily iron.

7. The process of claim 6 wherein the stabilized metal carbide catalyst comprises from about 10 to about 20 weight percent silicon, from about 0.5 to about 3 weight percent carbon and from about 77 to about 90.5 weight percent iron.

8. A process for the production of a fuel gas from a solid carbonaceous material comprising:
(a) reacting the solid carbonaceous material in a single fluidized reactor in the presence of a stabilized metal carbide catalyst comprising carbon and a metal alloy and having a free energy of formation of from −30,000 to 10,000 British thermal units per pound atom of carbon at the reaction conditions, said metal alloy comprising at least two metals selected from the group consisting of silicon, manganese, cobalt, chromium, nickel, aluminum, vanadium, tungsten, molybdenum, calcium, boron, sodium and magnesium, wherein one of said two metals forms a sufficiently stronger carbide to act as a stabilizing component thereby enhancing the chemical activity of the other metal carbide and wherein said metal alloy has a lower capacity for carburization and oxidation than each of the individual metals of the alloy and a fluidizing gas wherein from about 10 to about 30 volume percent of the fluidizing gas is selected from the group consisting of water vapor, carbon dioxide and mixtures thereof at a temperature of from about 500° C. to about 900° C. and a pressure of from about 100 kilopascals to about 8,300 kilopascals to produce a fuel gas containing methane;
(b) removing char produced in step (a) to a combustor and combusting it;
(c) removing a portion of the fuel gas produced in step (a) for recycle back to the reactor;
(d) removing a portion of the heat contained in the fuel gas produced in step (a) to heat water to produce water vapor and to heat a portion of the recycle gas;
(e) using the heat produced from the combustion of the char to further heat the water vapor and to further heat the recycle gas; and
(f) introducing the water vapor and the heated recycle gas into the reactor.

9. The process of claim 8 wherein the water vapor and recycle gas stream are combined and then heated with the heat produced from the combustion of the char.

10. The process of claim 8 wherein the temperature of the reactor is the threshold temperature range of the stabilized metal carbide catalyst.

11. The process of claim 10 wherein the stabilized metal carbide catalyst comprises from about 10 to about 20 weight percent silicon, from about 0.5 to about 3 weight percent carbon and from about 77 to about 90.5 weight percent iron, and wherein the threshold temperature of this stabilized metal carbide catalyst is from about 775° C. to about 845° C.

12. The process of claim 10 wherein the stabilized metal carbide catalyst is selected from the group consisting of iron silicide carbide, manganese chromium carbide, ferrochromium carbide and manganese cobalt carbide.

13. The process of claim 10 wherein the stabilized metal carbide catalyst is an iron silicide carbide comprising from about 4 to about 50 weight percent silicon, from about 0.5 to about 3 weight percent carbon and the remainder of the catalyst comprises primarily iron.

14. A process for the production of a fuel gas from a solid carbonaceous material comprising reacting in a single reaction zone the solid carbonaceous material in the presence of a stabilized metal carbide catalyst having a free energy of formation of from −30,000 to 10,000 British thermal units per pound atom of carbon at the reaction conditions, said metal alloy comprising at least two metals selected from the group consisting of iron, silicon, manganese, cobalt, chromium, nickel, aluminum, vanadium, tungsten, molybdenum, calcium, boron, sodium and magnesium, wherein one of said two metals forms a sufficiently stronger carbide to act as a stabilizing component thereby enhancing the chemical activity of the other metal carbide, said catalyst having characteristics of a bulk chemical catalyst and capable of substantially maintaining its physical integrity and chemical activity under gasification conditions, and a gas of which from about 10 to about 30 volume percent is selected from the group consisting of water vapor, carbon dioxide and mixtures thereof under reaction conditions to cause the formation of carbon monoxide, carbon dioxide, hydrogen and methane wherein the heat produced by the formation of carbon dioxide and methane is directly used to supply heat needed for the formation of hydrogen and carbon monoxide and wherein a sufficient amount of methane is formed to produce fuel gas wherein the temperature is from about 500° C. to about 900° C. and the pressure is from about 100 kilopascals to about 8300 kilopascals.

15. A process for the production of a fuel gas from a solid carbonaceous material comprising reacting in a single reaction zone the solid carbonaceous material in the presence of a stabilized metal carbide catalyst comprising a carbon and a metal alloy and having a free energy of formation of from −30,000 to 10,000 British thermal units per pound atom of carbon at the reaction conditions, said metal alloy comprising at least two metals selected from the group consisting of iron, silicon, manganese, cobalt, chromium, nickel, aluminum, vanadium, tungsten, molybdenum, calcium, boron, sodium and magnesium, wherein one of said two metals forms a sufficiently stronger carbide to act as a stabilizing component thereby enhancing the chemical activity of the other metal carbide, said catalyst having characteristics of a bulk chemical catalyst and capable of substantially maintaining its physical integrity and chemical activity under gasification conditions and a gas mixture comprising hydrogen, carbon monoxide and from about 10 to about 30 volume percent of gas selected from the group consisting of water vapor, carbon dioxide and mixtures thereof at a temperature and pressure sufficient to cause the gasification of the carbonaceous material and cause the formation of a sufficient amount of methane to produce a fuel gas having a Btu value greater than about 300 Btu per cubic foot of fuel gas, wherein a portion of the hydrogen and carbon monoxide is obtained by recycling a portion of the methane and the recycled gas is reformed to hydrogen and carbon monoxide by the addition of heat and water wherein the temperature is from about 500° C. to about 900° C. and the pressure is from about 100 kilopascals to about 8300 kilopascals.

16. The process of claim 14 wherein the stabilized metal carbide catalyst is selected from the group consisting of iron silicide carbide, manganese, chromium carbide, ferrochromium carbide and manganese cobalt carbide.

17. The process of claim 16 wherein the stabilized metal carbide catalyst is an iron silicide carbide comprising from about 4 to about 50 weight percent silicon, from about 0.5 to about 3 weight percent carbon and the remainder of the catalyst comprises primarily iron and wherein the temperature of the process is the threshold temperature range of the stabilized metal carbide catalyst.

18. The process of claim 17 wherein the Btu value of the fuel gas produced is greater than 400.

19. A process for the production of a fuel gas from a solid carbonaceous material comprising:
(a) reacting the solid carbonaceous material in a single reactor in the presence of a stabilized metal carbide catalyst capable of maintaining its physical integrity and chemical activity under gasification conditions, said catalyst comprising carbon and a metal alloy and having a free energy of formation of from −30,000 to 10,000 British thermal units per pound atom of carbon at the reaction conditions, said metal alloy comprising at least two metals selected from the group consisting of iron, silicon, manganese, cobalt, chromium, nickel, aluminum, vanadium, tungsten, molybdenum, calcium, boron, sodium and magnesium, wherein one of said two metals forms a sufficiently stronger carbide to act as a stabilizing component thereby enhancing the chemical activity of the other metal carbide, and a gas mixture comprising hydrogen, carbon monoxide and from about 10 to about 30 volume percent of a gas selected from the group consisting of water vapor, carbon dioxide and mixtures thereof at a temperature of from about 500° C. to about 900° C. and a pressure of from about 100 kilopascals to about 8,300 kilopascals to produce a fuel gas containing methane;

(b) removing char produced in step (a) to a combustor and combusting it;

(c) removing a portion of the fuel gas produced in step (a) for recycle back to the reactor;

(d) removing a portion of the heat contained in the fuel gas produced in step (a) to heat a water stream and to heat a portion of the recycle gas;

(e) combining the heated water stream and the heated recycle gas;

(f) using the heat produced from the combustion of the char to further heat the combined water and recycle gas stream to form water vapor and to reform a portion of the methane contained in the recycle gas to increase its level of hydrogen and carbon monoxide; and (g) introducing the combined stream of step (f) into the reactor.

20. A process for the production of a fuel gas from a solid carbonaceous material comprising reacting in a single reaction zone the solid carbonaceous material in the presence of a stabilized metal carbide catalyst comprising carbon and a metal alloy and having a free energy of formation of from −30,000 to 10,000 British thermal units per pound atom of carbon at the reaction conditions, said metal alloy comprising at least two metals selected from the group consisting of iron, silicon, manganese, cobalt, chromium, nickel, aluminum, vanadium, tungsten, molybdenum, calcium, boron, sodium and magnesium, wherein one of said two metals forms a sufficiently stronger carbide to act as a stabilizing component thereby enhancing the chemical activity of the other metal carbide, said catalyst having characteristics of a bulk chemical catalyst and capable of substantially maintaining its physical integrity and chemical activity under gasification conditions and a gas mixture comprising hydrogen, carbon monoxide and from about 10 to about 30 volume percent of a gas selected from the group consisting of water vapor, carbon dioxide and mixtures thereof at a temperature of from about 500° C. to about 900° C. and a pressure of from about 100 kilopascals to about 8,300 kilopascals under conditions which maintain the ratio of the reactant gases and product gases in order to cause the gasification of the carbonaceous material and the formation of a sufficient amount of methane to produce a fuel gas having a Btu value of from about 400 to about 450 Btu per cubic foot of fuel gas while maintaining the activity of the stabilized metal carbide catalyst.

21. The process of claim 19 or claim 20 wherein the temperature of the reactor is the threshold temperature range of the stabilized metal carbide catalyst.

22. The process of claim 21 wherein the stabilized metal carbide catalyst is selected from the group consisting of iron silicide carbide, manganese, chromium carbide, ferrochromium carbide and manganese cobalt carbide.

23. The process of claim 22 wherein the stabilized metal carbide catalyst is an iron silicide carbide catalyst comprising from about 4 to about 50 weight percent silicon, from about 0.5 to about 3 weight percent carbon and the remainder of the catalyst comprises primarily iron.

24. A process for the production of a fuel gas from a solid carbonaceous material comprising:

(a) reacting the solid carbonaceous material in a single reactor in the presence of a stabilized metal carbide catalyst capable of maintaining its physical integrity and chemical activity under gasification conditions, with a gas comprising hydrogen and, carbon monoxide and from about 10 to about 30 volume percent of the gas is selected from the group consisting of water vapor, carbon dioxide and mixtures thereof at a temperature of from about 500° C. to about 900° C. and a pressure of from about 100 kilopascals to about 8,300 kilopascals, wherein the stabilized metal carbide catalyst comprises carbon and a metal alloy and has a free energy of formation of from −30,000 to 10,000 British thermal units per pound atom of carbon at the reactor conditions, said metal alloy comprising at least two metals selected from the group consisting of iron, silicon, manganese, cobalt, chromium, nickel, aluminum, vanadium, tungsten, molybdenum, calcium, boron, sodium and magnesium wherein one of said two metals forms a sufficiently stronger carbide to act as a stabilizing component thereby enhancing the chemical activity of the other metal carbide, and wherein the reactant gases and product gases are maintained at ratios which allow for the gasification of the carbonaceous material and the formation of a sufficient amount of methane to produce a fuel gas having a Btu value of at least about 400 Btu per cubic foot of fuel gas;

(b) removing char produced in step (a) to a combustor and combusting it;

(c) removing a portion of the fuel gas produced in step (a) for recycle back to the reactor;

(d) removing a portion of the heat contained in the fuel gas produced in step (a) to heat a water stream and to heat a portion of the recycle gas;

(e) reforming the recycle gas stream of step (c) to obtain higher levels of hydrogen and carbon monoxide;

(f) using the heat produced from the combustion of the char to further heat the water vapor and to further heat the recycle gas to aid in reforming the methane contained in the recycle gas to hydrogen and carbon monoxide; and (g) introducing the water vapor and the reformed recycle gas into the reactor.

25. The process of claim 24 wherein the temperature of the reactor is the threshold temperature range of the stabilized metal carbide catalyst and the stabilized metal carbide catalyst is selected from the group consisting of iron silicide carbide, manganese chromium carbide, ferrochromium carbide and manganese cobalt carbide.

26. A process for the production of a fuel gas from a solid carbonaceous material comprising reacting in a single fluidized reaction zone the solid carbonaceous material in the presence of a stabilized metal carbide catalyst comprising carbon and a metal alloy and having a free energy of formation of from −30,000 to 10,000 British thermal units per pound atom of carbon at the reaction conditions, said metal alloy comprising at least two metals selected from the group consisting of iron, silicon, manganese, cobalt, chromium, nickel, aluminum, vanadium, tungsten, molybdenum, calcium, boron, sodium and magnesium, wherein one of said two metals forms a sufficiently stronger carbide thereby enhancing the chemical activity of the other metal carbide and a lower capacity for carburization and oxidation than each of the individual metals of the alloy and a fluidizing gas wherein from about 10 to about 30 volume percent of the fluidizing gas is selected from the group consisting of water vapor, carbon dioxide and mixtures thereof at a temperature and pressure sufficient to carbide the stabilized metal alloy, to cause the gasification of the carbonaceous material and cause the formation of a sufficient amount of methane to produce a fuel gas having a Btu value greater than about 300 Btu per cubic foot of fuel gas wherein the temperature is from about 500° C. to about 900° C. and the pressure is from about 100 kilopascals to about 8300 kilopascals.

27. A process for the production of a fuel gas from a solid carbonaceous material comprising:
(a) reacting the solid carbonaceous material in a single reactor in the presence of a stabilized metal carbide catalyst comprising at least two metals selected from the group consisting of iron, silicon, manganese, cobalt, chromium, nickel, aluminum, vanadium, tungsten, molybdenum, calcium, boron, sodium and magnesium, wherein one of said two metals forms a sufficiently stronger carbide to act as a stabilizing agent thereby enhancing the chemical activity of the other metal carbide and having a lower capacity for carburization and oxidation than each of the individual metals of the alloy and a gas wherein from about 10 to about 30 volume percent of the gas is selected from the group consisting of water vapor, carbon dioxide and mixtures thereof at a temperature of from about 500° C. to about 900° C. and a pressure of from about 100 kilopascals to about 8,300 kilopascals to cause the carbiding of the stabilized metal alloy, to cause the gasification of the carbonaceous material and the formation of a sufficient amount of methane in order to obtain a fuel gas having a fuel value of at least 300 Btu per cubic foot of fuel gas, said metal carbide catalyst being formed at said conditions by the carbidizing of said metal alloy;
(b) removing char produced in step (a) to a combustor and combusting it;
(c) removing a portion of the gas produced in step (a) to a combustor and combusting it;
(d) removing a portion of the heat contained in the gas produced in step (a) to heat water to produce water vapor and to heat a portion of the recycle gas;
(e) using the heat produced from the combustion of the char to further heat the water vapor and to further heat the recycle gas; and
(f) introducing the water vapor and the reformed recycle gas into the reactor.

* * * * *